(12) United States Patent
Rafferty et al.

(10) Patent No.: US 9,312,112 B2
(45) Date of Patent: Apr. 12, 2016

(54) EVACUATING A SAMPLE CHAMBER

(75) Inventors: David Rafferty, Webster, TX (US);
James Wylde, Oak Leaf, TX (US);
Michael Spencer, Manvel, TX (US);
Pedro Ojeda, Pflugerville, TX (US)

(73) Assignee: 1ST DETECT CORPORATION, Austin, TX (US)

( * ) Notice: Subject to any disclaimer, the term of this patent is extended or adjusted under 35 U.S.C. 154(b) by 256 days.

(21) Appl. No.: 13/348,390

(22) Filed: Jan. 11, 2012

(65) Prior Publication Data
US 2012/0180576 A1 Jul. 19, 2012

Related U.S. Application Data

(60) Provisional application No. 61/432,123, filed on Jan. 12, 2011.

(51) Int. Cl.
*G01N 1/44* (2006.01)
*H01J 49/04* (2006.01)
*G01N 1/40* (2006.01)

(52) U.S. Cl.
CPC ............... *H01J 49/049* (2013.01); *G01N 1/405* (2013.01)

(58) Field of Classification Search
CPC ............... G01N 1/405; G01N 1/2214; G01N 2004/022; G01N 2001/028; G01N 2001/022; B01L 2300/10; B01L 2300/1827; B01L 2400/049; H01J 49/049
USPC ............... 73/863.11, 863.12, 864.81–864.85, 73/864.91, 864.71
See application file for complete search history.

(56) References Cited

U.S. PATENT DOCUMENTS

| | | | |
|---|---|---|---|
| 5,256,874 A | 10/1993 | Chutjian | |
| 5,741,984 A * | 4/1998 | Danylewych-May et al. | 73/864.71 |
| 6,884,997 B2 * | 4/2005 | Kashima et al. | 250/288 |
| 7,002,145 B2 * | 2/2006 | Ishikawa et al. | 250/288 |
| 7,299,710 B2 * | 11/2007 | Syage | 73/863.12 |
| 7,669,487 B2 * | 3/2010 | Luke et al. | 73/863.12 |
| 7,997,119 B2 * | 8/2011 | Wu | 73/31.03 |
| 8,161,830 B2 * | 4/2012 | Boudries et al. | 73/863.12 |
| 8,291,777 B2 * | 10/2012 | Tovena-Pecault | 73/863.12 |
| 8,756,975 B2 * | 6/2014 | Wu | 73/31.05 |
| 2002/0066857 A1 * | 6/2002 | Hughey et al. | 250/281 |

(Continued)

FOREIGN PATENT DOCUMENTS

GB 2262603 A 6/1993
JP 11287743 A 10/1999

OTHER PUBLICATIONS

Authorized Officer Pierre Loiseleur, International Search Report and the Written Opinion of the International Searching Authority for Application No. PCT/US2012/020934 dated Jun. 27, 2012, 10 pages.

*Primary Examiner* — Peter Macchiarolo
*Assistant Examiner* — Natalie Huls
(74) *Attorney, Agent, or Firm* — Finnegan, Henderson, Farabow, Garrett & Dunner LLP

(57) ABSTRACT

In one general aspect, a sample is transferred into a mass spectrometer by capturing a sample on a collector, inserting the collector into a sample chamber coupled to the mass spectrometer and a vacuum pump, evacuating the sample chamber using the vacuum pump to reduce an internal pressure of the sample chamber to a level less than atmospheric pressure, heating the collector to release the sample from the collector, and introducing the sample into the mass spectrometer from the evacuated sample chamber.

29 Claims, 11 Drawing Sheets

(56) References Cited

U.S. PATENT DOCUMENTS

| | | |
|---|---|---|
| 2004/0124352 A1 | 7/2004 | Kashima et al. |
| 2004/0195499 A1* | 10/2004 | Ishikawa et al. ............... 250/281 |
| 2005/0109932 A1* | 5/2005 | Mullock et al. ................ 250/288 |
| 2006/0219893 A1* | 10/2006 | Nishihira et al. .............. 250/288 |
| 2006/0226358 A1* | 10/2006 | Ishikawa et al. ............... 250/307 |
| 2009/0090197 A1* | 4/2009 | Finlay et al. ................ 73/863.12 |
| 2009/0249897 A1* | 10/2009 | Doring et al. ............... 73/864.71 |
| 2009/0293647 A1* | 12/2009 | Muneishi et al. .......... 73/864.11 |
| 2011/0283776 A1* | 11/2011 | Wu ............................... 73/31.05 |
| 2012/0223226 A1* | 9/2012 | Rafferty et al. ............... 250/288 |
| 2012/0270334 A1* | 10/2012 | Ojeda et al. .................... 436/178 |

\* cited by examiner

EVACUATING A SAMPLE CHAMBER

CROSS-REFERENCE TO RELATED APPLICATIONS

This application claims the benefit of priority to U.S. Provisional Application Ser. No. 61/432,123, filed on Jan. 12, 2011, which is incorporated by reference herein.

TECHNICAL FIELD

This disclosure is related to the field of chemical analysis and detection, and more particularly to the use of a sample collection and introduction system that utilizes a sample collector inserted into a sample chamber and chamber evacuation techniques to increase the concentration of a sample introduced to a detection device such as a mass spectrometer.

BACKGROUND

Chemical analysis tools such as gas chromatographs ("GC"), mass spectrometers ("MS"), ion mobility spectrometers ("IMS"), and various others, are commonly used to identify trace amounts of chemicals, including, for example, chemical warfare agents, explosives, narcotics, toxic industrial chemicals, volatile organic compounds, semi-volatile organic compounds, hydrocarbons, airborne contaminants, herbicides, pesticides, and various other hazardous contaminant emissions.

Most explosives, however, have very low volatility indices and as such, emit a very low amount of vapor into the surrounding air, typically below the detection limit of most analysis instruments. For this reason, detection typically involves the use of a swab or pad to capture the sample, and in some cases, involves heating the collector to release or vaporize the sample, thereby releasing it into an ambient gas matrix (e.g., air) before being transferred into the chemical detector.

SUMMARY

Implementations of the present disclosure are directed to devices, systems, and techniques for facilitating the rapid detection of particulates or chemicals captured in a collector (e.g., a swab, pad, cloth, wipe, vial, substrate) by increasing the effective concentration of the sample as seen by a chemical detector. In one general aspect, the effective concentration of a sample captured in or on a collector is increased by enclosing the collector in a sample chamber, evacuating the chamber to reduce an internal pressure of the chamber to a level substantially less than the pressure of the surrounding atmosphere, heating the collector to release the sample, and introducing the sample into the mass spectrometer.

In another general aspect, transferring a sample into a mass spectrometer is accomplished by capturing a sample on a collector; inserting the collector into a sample chamber coupled to the mass spectrometer and a vacuum pump; evacuating the sample chamber using the vacuum pump to reduce an internal pressure of the sample chamber to a level less than atmospheric pressure; heating the collector to release the sample from the collector; and introducing the sample into the mass spectrometer from the evacuated sample chamber.

In yet another general aspect, a sample analysis system includes a sample chamber configured to receive a collector carrying a sample, the sample chamber including a base and a lid operable to access a cavity formed by the base and the lid; a vacuum pump coupled to the sample chamber and configured to evacuate the sample chamber to reduce an internal pressure of the sample chamber to a level less than atmospheric pressure; a heating element configured to heat the collector to release the sample from the collector into the evacuated sample chamber; and a chemical analyzer coupled to the sample chamber and configured to receive the sample from the evacuated sample chamber.

In another general aspect, a sample chamber includes a base and a lid forming a cavity configured to receive a collector carrying a sample; and a heating element configured to heat the collector to release the sample from the collector; wherein the sample chamber is configured to be coupled to a vacuum pump operable to evacuate the sample chamber to reduce an internal pressure of the sample chamber to a level less than atmospheric pressure prior to the release of the sample from the collector.

These and other implementations may each optionally include one or more of the following features: the collector can include a sorbent material; capturing the sample on the collector may include wiping a surface of a target object with the collector, depositing the sample on the collector, or submerging at least a portion of the collector into a target substance; inserting the collector into the sample chamber may include forming a substantially air-tight seal around the collector when inserted into the sample chamber and/or pressing the collector against a heating element; heating the collector may include conducting current through a heating element to induce Joule heating; determining a temperature of the collector based on a measured resistance of the heating element; heating the collector may include emitting radiant energy substantially toward the collector using one or more heating elements, and/or reflecting the emitted radiant energy substantially toward the collector using a reflective barrier; the radiant heating element may be configured to emit radiant energy of a particular wavelength that preferentially excites a sample of interest; the collector may be a wipe, a substrate, or a swab; the sample chamber may include one or more gaskets or seals positioned between the base and the lid to form a substantially air-tight seal around the collector when inserted into the sample chamber; the base and lid may be configured to press the collector against the heating element; the heating element can be configured to generate heat via Joule heating; the heating element can be configured to emit radiant energy substantially toward the collector; the system can include a reflective barrier configured to reflect the emitted radiant energy substantially toward the collector; the sample can include a first compound and a second compound, different from the first compound; heating the collector can include variably heating the collector over time, such that, in response to variably heating the collector, the first compound is primarily released during a first time period, and the second compound is primarily released during a second time period; variably heating the collector can include operating a resistive heating element or a radiant heating element at a first power level during the first time period and at a second power level during the second time period; variably heating the collector can include emitting radiant energy having a first radiant frequency substantially toward the collector during the first time period, and emitting radiant energy having a second radiant frequency substantially toward the collector during the second time period; evacuating the sample chamber using the vacuum pump to reduce the internal pressure of the sample chamber can include reducing the internal pressure of the sample chamber to a first level during a first time period, and reducing the internal pressure of the sample chamber to a second level during a second time period, such that, in response to heating the collector, the first compound is primarily released during the first time period and the second compound is primarily released during the second time period; introducing the sample into the mass spectrometer from the evacuated sample chamber can include primarily introducing the first compound during a first time period and primarily introducing the second compound during a second time period; the sample can include a first compound and a second compound, different from the first compound, and the heating element can be configured to variably heat the collector over time, such that, in response to variably heating the collector, release of the first compound is initiated during a first time period, and release of the second compound is initiated during a second time period the heating element is configured to operate at a first power level during the first time period and at a second power level during the second time period; the heating element can be configured to emit radiant energy having a first radiant frequency substantially toward the collector during the first time period, and can be configured to emit radiant energy having a second radiant frequency substantially toward the collector during the second time period; the vacuum pump can be configured to reduce the internal pressure of the sample chamber to a first level during a first time period, and to reduce the internal pressure of the sample chamber to a second level during a second time period, such that, in response to heating of the collector, release of the first compound is initiated during the first time period and release of the second compound is initiated during the second time period.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
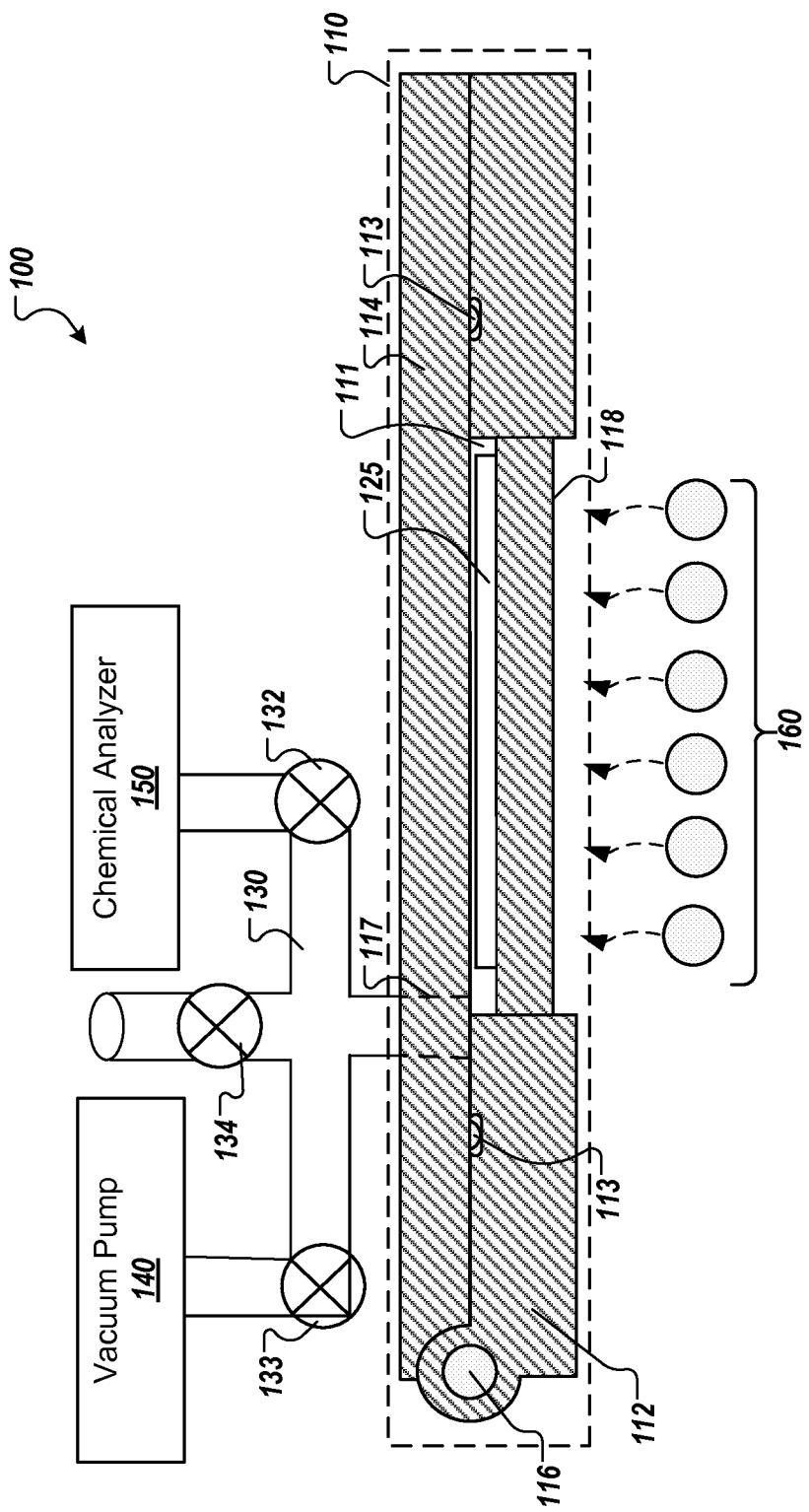
FIG. 1 is a system diagram of an exemplar chemical detection system.

In the description below, for the purposes of explanation, specific examples related to detecting particulates/chemicals captured in or on a collector and analyzed using a mass spectrometer have been set forth in order to provide a thorough understanding of the implementations of the subject matter described in this specification. It is appreciated that the implementations described herein can be utilized in other capacities as well and need not be limited to mass spectrometers, but may be used to improve the operation of other detection instruments and techniques used in series or in parallel with a mass spectrometer. Accordingly, other implementations are within the scope of the claims.

Mass spectrometers are particularly well suited for chemical analysis due to the high resolution measurements that can be realized and because mass spectrometers measure a fundamental property of chemicals that are introduced into the instrument. Other forms of chemical analysis instrumentation such as ion mobility spectrometers, surface acoustic wave devices, electrochemical cells, and similar instruments measure the constituents of a sample by inferring their presence from measurements of related phenomena such as resonant frequency changes, voltage changes, and drift time measurements. In addition, while other analytical instruments typically operate at approximately one atmosphere of pressure, mass spectrometers typically require a vacuum environment (e.g., pressures of $10^{-6}$-$10^{-3}$ Torr) for proper operation. Because mass spectrometers operate at pressures well below that of atmospheric pressure, fewer molecules are present per unit volume in the instrument than for those instruments that operate at higher pressures. This is well described by the Ideal Gas Law:

$$pV=nRT$$

where p is the pressure inside the analysis chamber of an instrument, V is the volume of the analysis chamber, n is the number of molecules present, R is a constant equal to 8.314 J mol$^{-1}$ K$^{-1}$, and T is the temperature of the sample.

In some applications, the number of molecules present is further decreased by miniaturization of the mass spectrometer (i.e., decreased V) to enable easy portability, for example, by airport security personnel. This is illustrated by the Ideal Gas Law noted above by decreasing both p and V; as a result, the number of molecules present, n, is reduced accordingly. Thus, the effect of reducing the detection volume of the instrument is a reduction in the sensitivity of the instrument, where the sensitivity is the minimum external amount of a sample that can be measured by the instrument. For example, a mass spectrometer operating at $10^{-3}$ Torr, with an analysis chamber volume of 1 mm$^3$, operating at 25° C. will have 32.3×10$^9$ molecules present. A corresponding instrument that operates at atmospheric pressure (760 Torr) will have 24.6×10$^{15}$ molecules present. A corresponding instrument that operates at $10^{-3}$ Torr but has an analysis chamber that is 1 cm$^3$ will have 32×10$^{12}$ molecules present. Thus, miniaturizing instruments that operate at lower pressures significantly reduces the number of molecules available for analysis.

As noted above, most explosives have very low volatility indices and as such, emit a very low amount of vapor into the surrounding air. For this reason, detection typically involves the use of a surface wipe, for example, to collect the sample, and in some cases, involves heating the collector to release or vaporize the sample, which may or may not decompose into more primitive components during the release/vaporization, into an ambient gas matrix (e.g., air) before being transferred into the chemical detector. However, if this sample is introduced into a miniature mass spectrometer, the chance of detecting the presence of a chemical of interest in that sample is thus significantly reduced. Nevertheless, techniques are available to those skilled in the art to improve the sensitivity of the instrument, including, for example, coupling a mass spectrometer with a gas chromatograph, and repeating the analysis multiple times. However, these and other techniques for improving the sensitivity of the instrument can significantly increase the analysis time, typically from several seconds to several minutes, or in the case of a gas chromatograph coupled to a mass spectrometer, up to 30 minutes, typically.

The present disclosure provides alternative techniques for improving the sensitivity of a mass spectrometer in detecting chemicals/particulates captured in a collector without a significant increase in analysis time. In particular, by enclosing the collector in a sample chamber and evacuating the chamber prior to the heating/analysis process, the effective concentration of the sample can be increased over that of a sample introduced from a non-evacuated chamber. The following explanation further illustrates this concept. For low partial pressures of analyte compared to partial pressures of background matrix, the gain due to the evacuation of the 'dead volume' within the sample chamber to a reduced pressure is given by:

$$G_{evacuation} = P_{ambient}/P_{evacuated},$$

assuming $P_{evacuated}$ is greater than the operating pressure of the chemical analyzer, where $P_{ambient}$ is the pressure within a typical sample chamber (i.e., ambient) and $P_{evacuated}$ is the reduced pressure in the sample chamber after evacuation. Table 1 below illustrates a sample calculation showing net gain that can be achieved by evacuation of the dead volume.

TABLE 1

| Evacuation Gain | |
|---|---|
| Typical Chamber Pressure ($P_{ambient}$) | 760 Torr |
| Evacuated Pressure ($P_{evacuated}$) | $10^{-2}$ Torr |
| Pressure Ratio | 76000 |
| Evacuation Gain ($G_{evacuation}$) | 76000 |

By evacuating the dead volume in the chamber prior to releasing or desorbing the sample, the effective concentration of the sample, as seen by the mass spectrometer, is substantially increased. In other words, by decreasing the number of background matrix molecules and simultaneously substantially maintaining the number of analyte molecules, the ratio of analyte molecules to the total number of molecules in the volume is effectively increased. In addition, by preventing a substantial portion of the background matrix and other airborne contaminants from entering the instrument, the accuracy of the analysis is typically improved.

In addition to improving the sensitivity of a mass spectrometer, evacuation of the sampling system improves the operation of the detection system by reducing contamination of the transfer path and/or the heat requirements for the transfer path. Explosives are very "sticky" compounds. When sampling explosive residues at atmospheric pressure, the transfer paths are typically heated to prevent the explosive vapors from sticking or condensing to the transfer lines. Compounds are much less likely to stick to or condense in a transfer path when the pressure in the transfer path is reduced to or near the vapor pressure of the compound in question and the temperature of the transfer path is near or above the corresponding boiling point, which will generally be much lower than the boiling point at atmospheric pressure. In general, the boiling point temperature of a compound decreases as the environmental pressure surrounding the compound decreases. Furthermore, by reducing the probability that compounds will condense along the transfer path, the evacuation of the sampling system in combination with the heating phase of the sampling process reduces or eliminates the need for lengthy purge cycles between samplings, thereby improving the system's purge efficiency.

FIG. 1 illustrates an exemplar chemical detection system (CDS) 100 configured to facilitate the rapid detection of particulates/chemicals at extremely low concentrations while reducing heat requirements for a transfer path between a sample chamber and a chemical detector and improving the system's purge efficiency. CDS 100 includes a sample chamber 110 (shown in cross-sectional form) having a base 112 and a lid 114. Base 112 and lid 114 define a substantially air-tight cavity 111 configured to receive a collector 125 containing a surface-wiped, adsorbed, or absorbed sample. In some implementations, base 112 and lid 114 are mechanically coupled, for example, by a hinge 116 (as shown in FIG. 1) or other similar mechanisms, such that the two portions can be separated to allow access to cavity 111 for the insertion and removal of collector 125.

Figure 2:
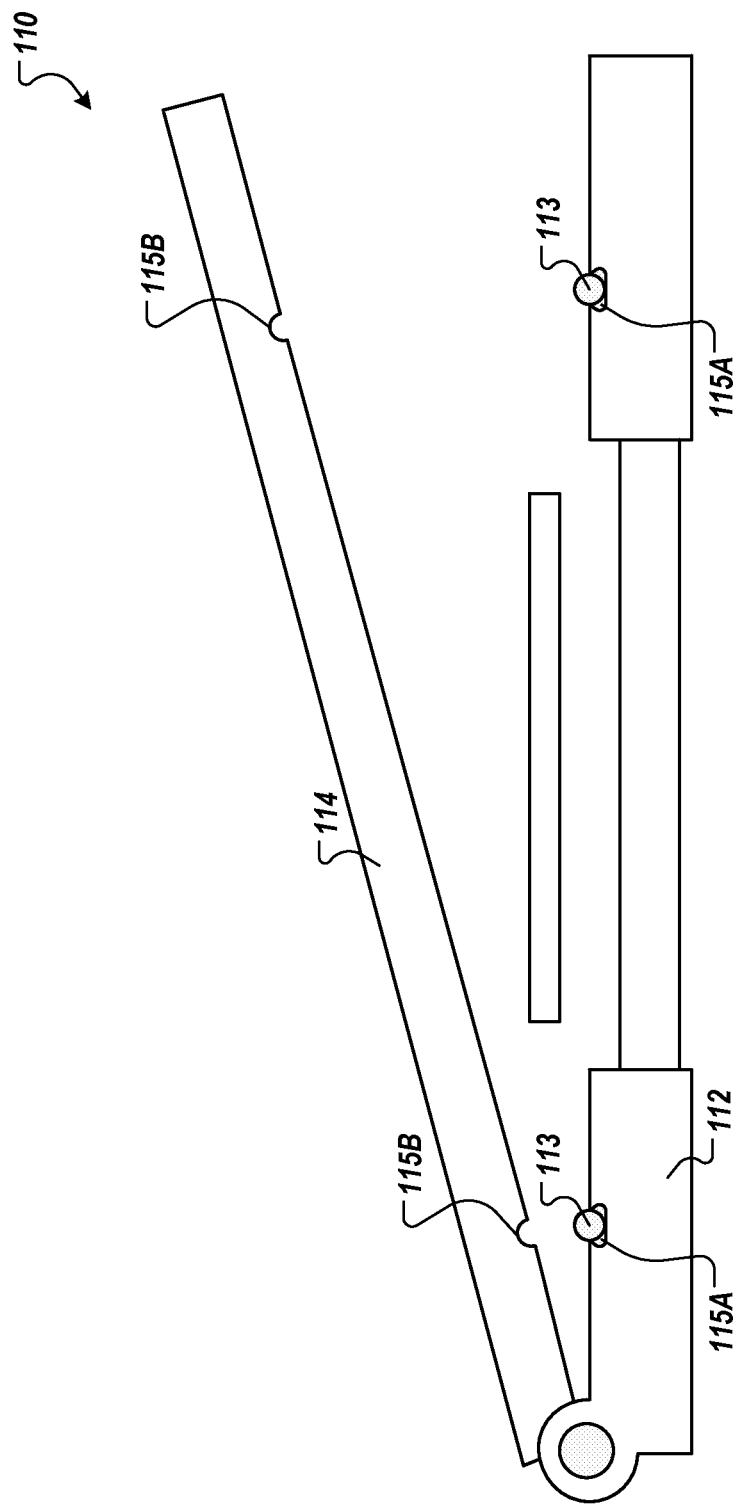
FIGS. 2, 3, and 4 are cross-sectional views of exemplar sample chambers.

When sample chamber 110 is closed, a substantially air-tight seal is formed between the base 112 and lid 114, for example, by one more gaskets or seals 113. FIG. 2 is a cross-section view of sample chamber 110 when opened. As shown in FIG. 2, in some implementations, gasket 113 is inserted in a groove 115A defined by base 112. Optionally, lid 114 may also define a groove 115B positioned opposite groove 115A to receive gasket or seal 113.

Figure 8:
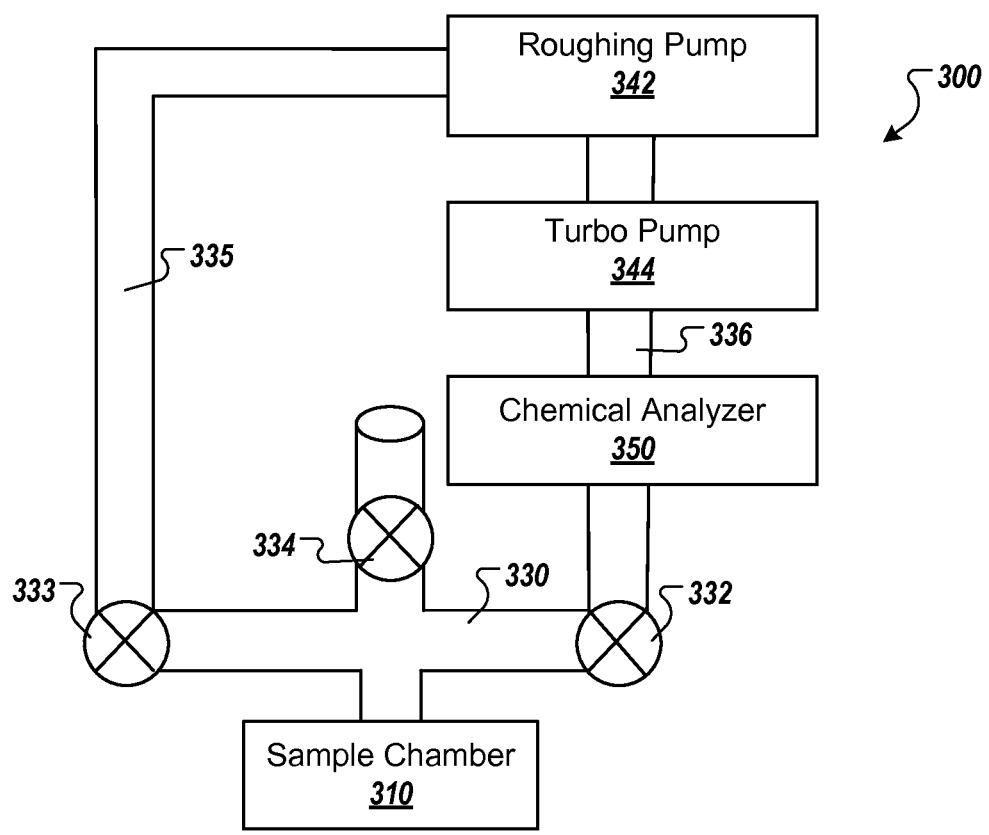
FIG. 8 is a system diagram of an exemplar arrangement of a chemical detection system.

Referring again to FIG. 1, sample chamber 110 is coupled to a vacuum path 130 via a vacuum port 117 defined by lid 114. In some examples, vacuum port 117 is defined by base 112, for example, to limit the flexing of vacuum plumbing forming vacuum path 130. In general, however, vacuum port 117 is located adjacent to cavity 111 to facilitate the evacuation of the dead volume within the cavity by a vacuum pump 140 coupled to vacuum path 130 via a valve 133. Vacuum path 130 is also coupled to a chemical analyzer 150 via a valve 132. Valve 132 is operable to isolate an inlet port or analysis chamber of chemical analyzer 150 from sample chamber 110, for example, before the evacuation of the dead volume within the cavity. Valve 134 is operable to re-pressurize sample chamber 110 after the analysis to allow an operator to open the sample chamber, extract the collector, and insert the next sample. Other arrangements are also possible, including, for example, evacuating sample chamber 110 using a vacuum pump system coupled directly to chemical analyzer 150, or evacuating sample chamber 110 via a separate vacuum path coupled to vacuum pump 140. FIG. 8, as described below, illustrates another possible arrangement.

After cavity 111 has been evacuated, the sample is released by heating collector 125. In some implementations, heating of the collector 125 is accomplished by utilizing infrared heating elements 160, as illustrated in FIG. 1. The infrared heating elements are positioned so that they emit radiant energy substantially toward collector 125 through a substrate 118 (e.g., fused quartz window) forming a portion of base 112. In some implementations, one or more infrared wavelengths are chosen to preferentially excite particular compounds of interest. Other techniques or materials may also be used to effect the release or vaporization of the sample from collector 125, including, for example, the use of a conductive heating element heated by Joule heating, described in more detail below. In alternative implementations electrical current is passed through an electrically conductive collector, such as a carbon cloth, in order to heat the collector and release the analyte.

In some examples, the heating element is controlled such that the temperature imparted upon the collector, which may contain a plurality of analytes (e.g., compounds of interest) having different boiling points at the pressure present in cavity 111, allows one or more of the analytes to be released while retaining one or more analytes. In some implementations, the temperature of collector 125 is adjusted in a pattern, and valve 132 is operated, such that analytes are released and introduced into chemical analyzer 150 at different times. In some examples, the pressure of cavity 111 is adjusted in a pattern, with either substantially constant temperature or a corresponding temperature profile, to allow selective release of analyte from collector 125. The analyte can be released via a variety of mechanisms, including, for example, controlling the temperature of a conductive heating element by adjusting voltage and current, and hence energy density (Joule heating), adjusting the frequency, wavelength, or intensity of a radiant source (for example infrared diodes), modulating the pulse width and/or frequency of a radiant source (PWM), and similar techniques. Other techniques for adjusting the temperature of collector 125 can be realized without changing the scope of this disclosure.

Figure 3:
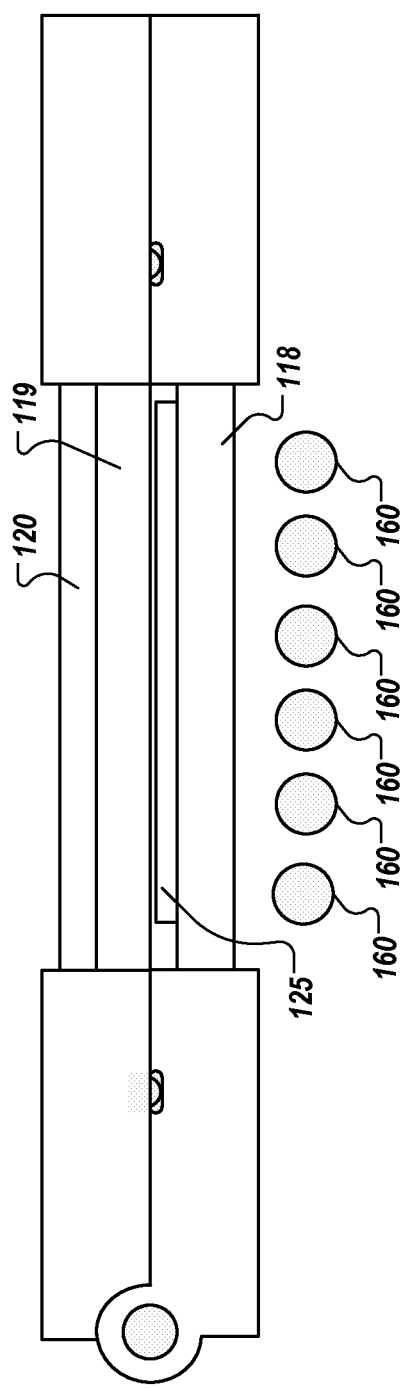
Figure 4:
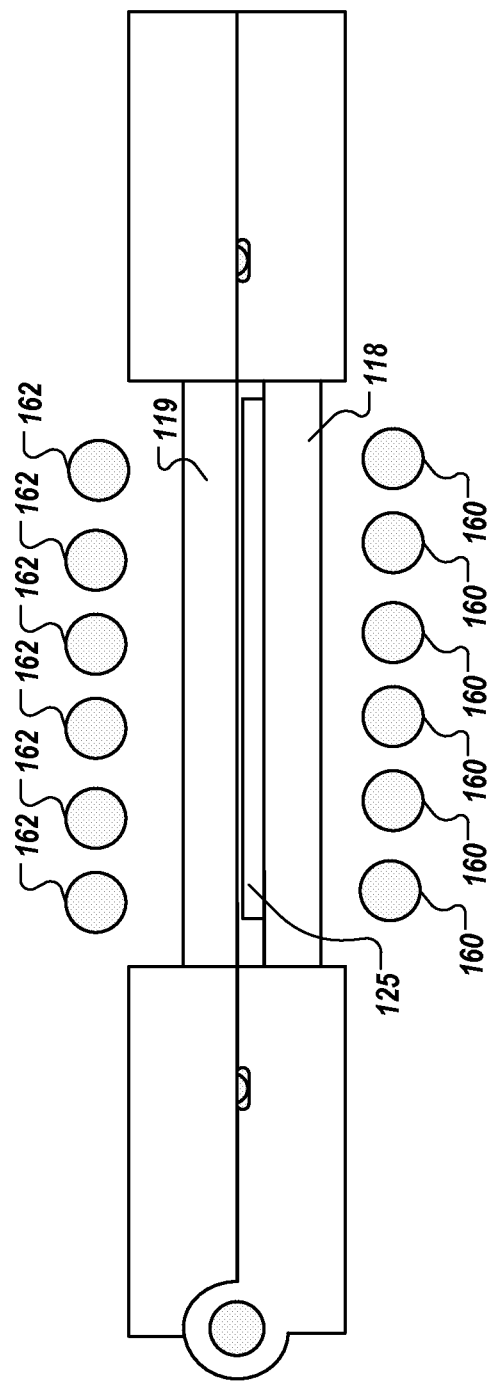

FIGS. 3 and 4 illustrate alternative implementations of sample chamber 110 in which lid 114 includes a substrate 119 (e.g., fused quartz window). As illustrated in FIG. 3, in some implementations, substrate 119 includes mirror backing 120 such that radiant energy emitted by infrared heating elements 160 is reflected back towards collector 125. FIG. 4 illustrates another alternative implementation in which a second set of infrared heating elements 162 is positioned adjacent substrate 119 so that they emit radiant energy substantially toward collector 125 through substrate 119. In some implementations, infrared heating elements 160 are embedded or included in base 112 and/or lid 114.

Figure 5:
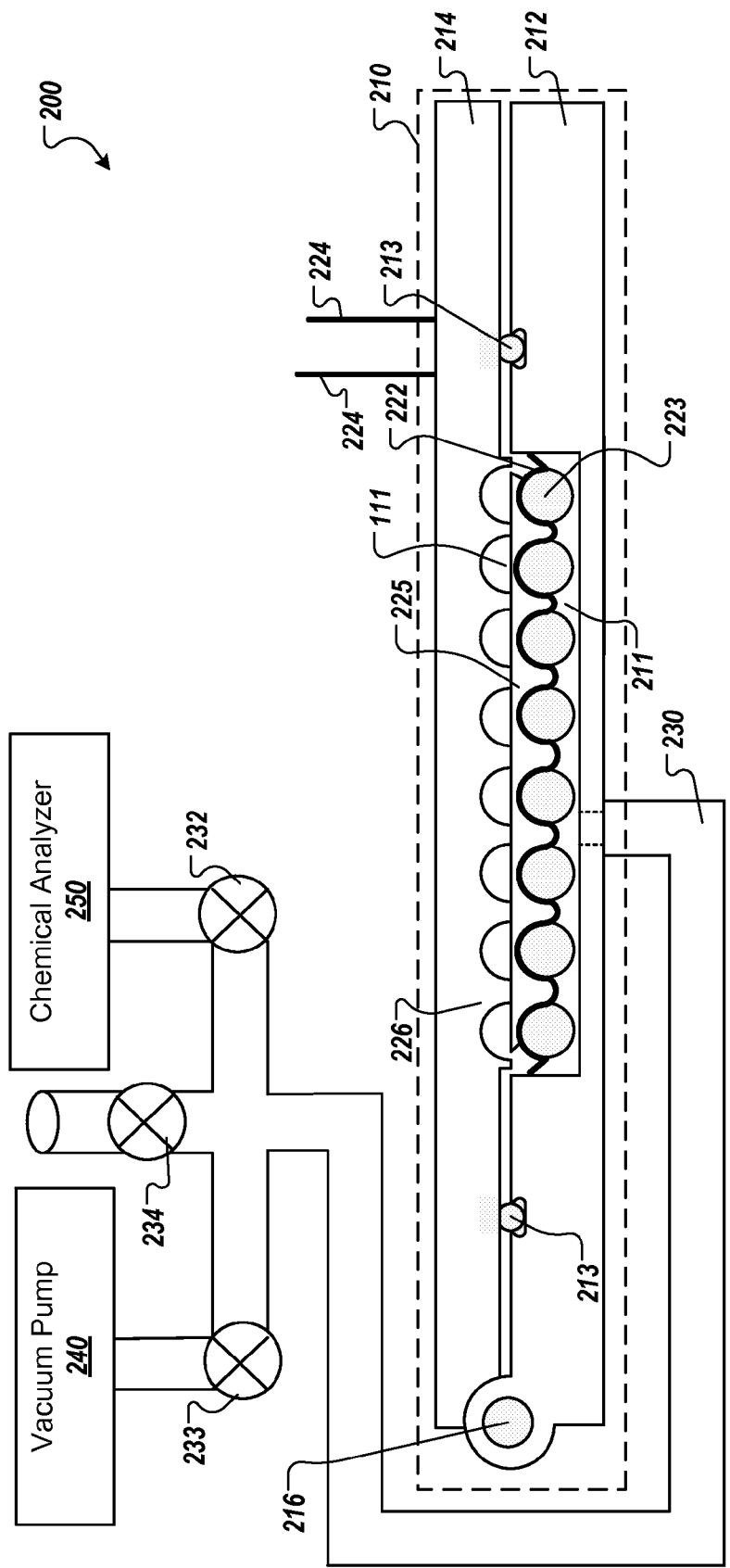
FIG. 5 is a system diagram of another exemplar chemical detection system.

FIG. 5 illustrates another exemplar chemical detection system (CDS) 200 configured to facilitate the rapid detection of chemicals at extremely low concentrations while reducing heat requirements for a transfer path between a sample chamber and a chemical detector and improving the system's purge efficiency. CDS 200 includes a sample chamber 210 (shown in cross-sectional form) having a base 212 and a lid 214. Base 212 and lid 214 define a substantially air-tight cavity 211 configured to receive a collector 225 containing a surface-wiped sample. Similar to CDS 100, in some implementations, base 212 and lid 214 are mechanically coupled, for example, by a hinge 216 (as shown in FIG. 4) or other similar mechanisms, such that the two portions can be separated to allow access to cavity 211 for the insertion and removal of collector 225. When sample chamber 210 is closed, a substantially air-tight seal is formed between the base 212 and lid 214, for example, by gasket 213.

Figure 6A:
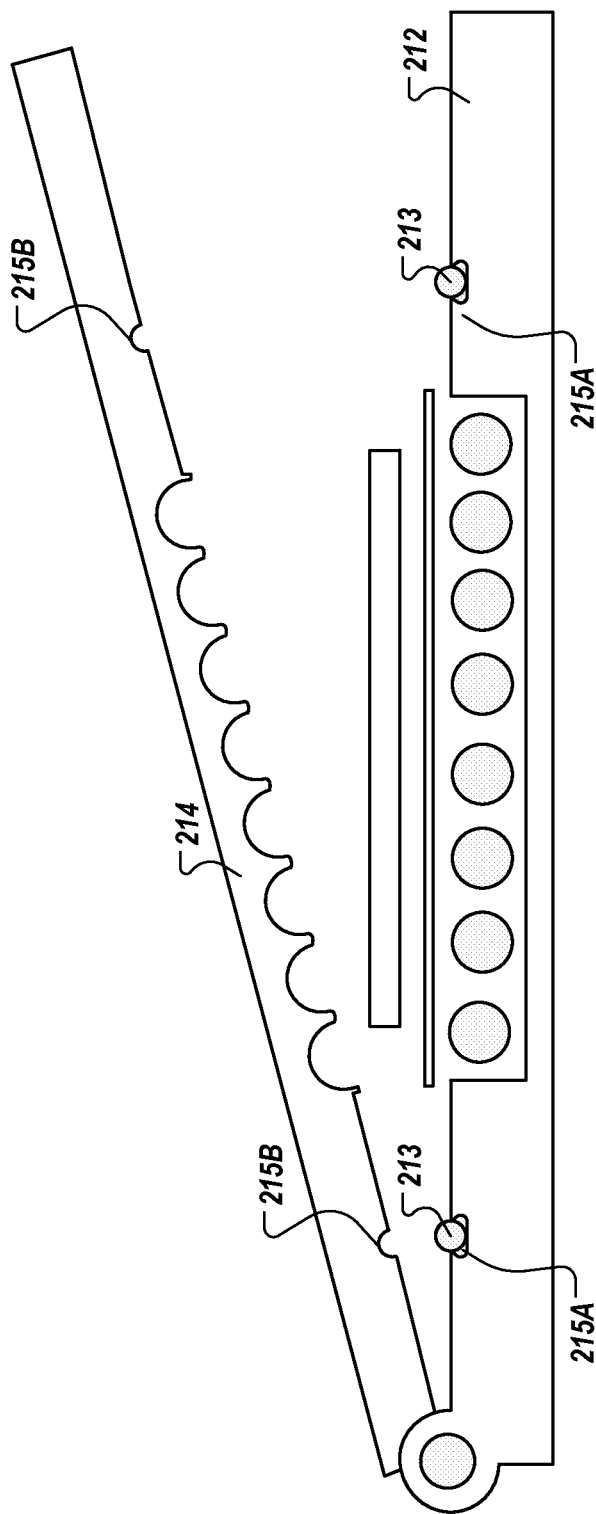
FIGS. 6A-6C are perspective and cross-sectional views of an exemplar sample chamber.
Figure 6B:
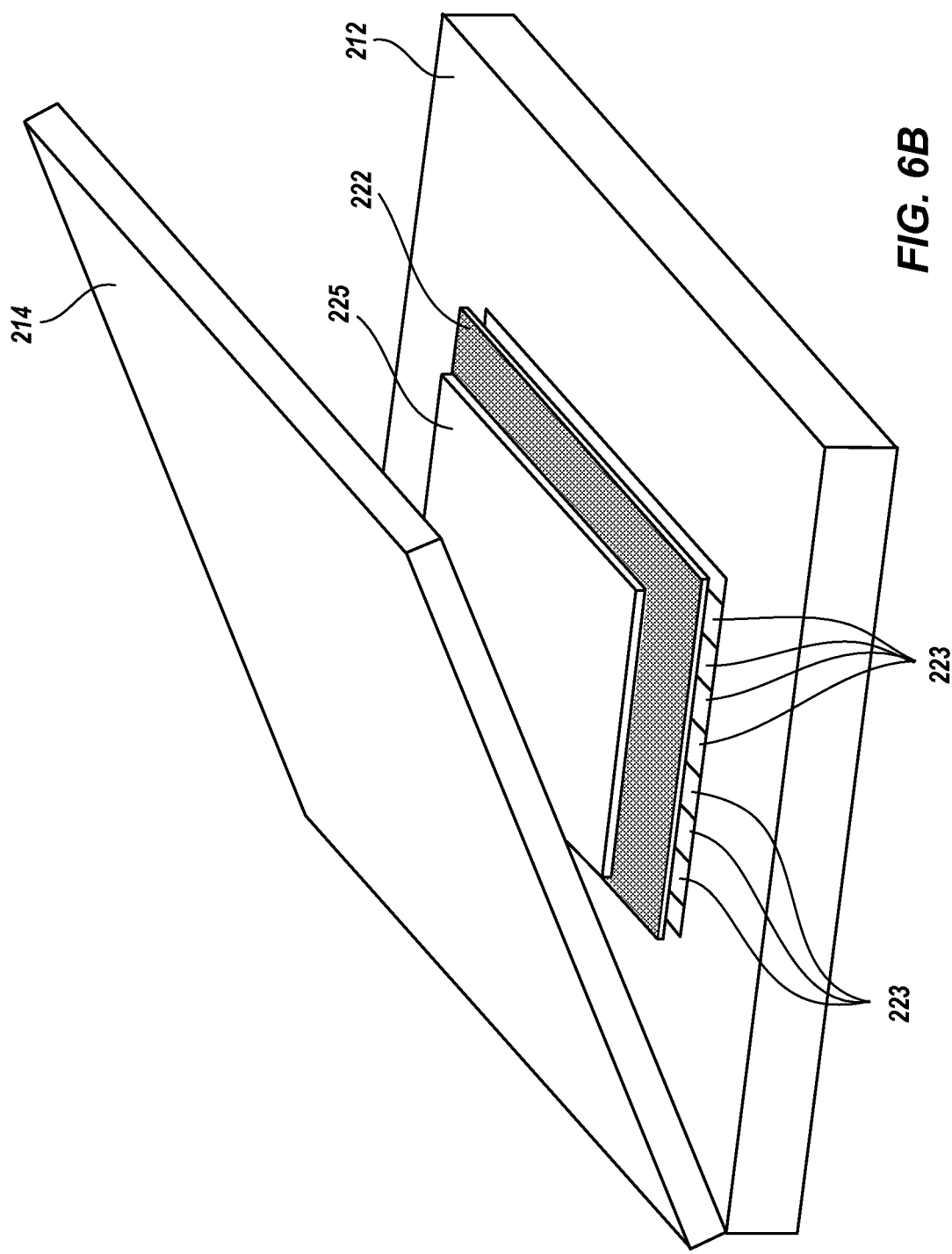
Figure 6C:
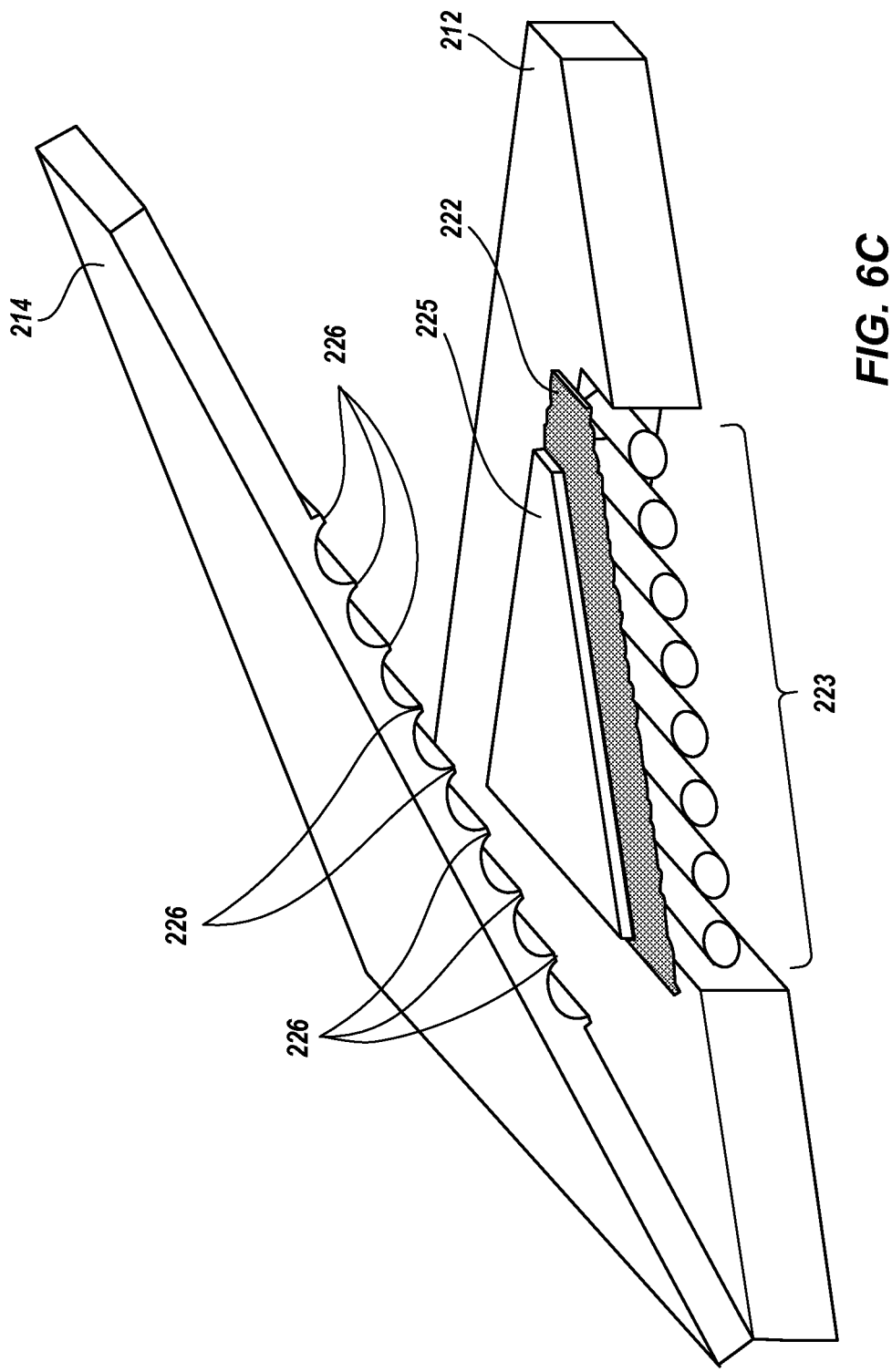

FIGS. 6A-6C are perspective/cross-sectional views of sample chamber 210 when opened. As shown in FIG. 6A, in some implementations, gasket or seal 213 is inserted in a groove 215A defined by base 212. Optionally, lid 214 may also define a groove 215B positioned opposite groove 215A to receive gasket or seal 213.

Referring again to FIG. 5, sample chamber 210 is coupled to vacuum path 230 and vacuum pump 240 via valve 233 and a vacuum port 217 defined by base 212 to facilitate the evacuation of the dead volume within cavity 211. Vacuum path 230 is also coupled to a chemical analyzer 250 via a valve 232. Valve 232 is operable to isolate the analysis chamber of chemical analyzer 250 from sample chamber 210, for example, before the evacuation of the dead volume within the cavity. After cavity 211 has been evacuated, valve 232 is opened and the sample is released or vaporized by heating collector 225. In some implementations, valve 232 remains closed until the completion of the heating phase. Valve 234 is operable to re-pressurize sample chamber 210 after the analysis to allow an operator to open the sample chamber, extract the collector, and insert the next sample. As discussed above with regard to FIG. 1, other arrangements are also possible, including, for example, evacuating sample chamber 210 using a vacuum pump coupled directly to chemical analyzer 250, or evacuating sample chamber 210 via a separate vacuum path coupled to vacuum pump 240. FIG. 8, as described below, illustrates another possible arrangement.

As illustrated in FIG. 5, sample chamber 210 includes a conductive heating element 222 (e.g., a NiChrome mesh) configured to provide rapid heating of collector 125 via close contact with the collector. For example, in some implementations, conductive heating element 222 is supported by support rods 223 formed within cavity 211 in base 212. Lid 214 defines a set of ridges 226 running parallel to support rods 223 and aligned so as to compress collector 225 and conductive heating element 222 against support rods 223 when sample chamber 210 is closed. In some implementations, conductive heating element 222 is coupled to electrical leads 224 such that a current supplied through electrical leads 224 results in resistive heating or Joule heating of the heating element. Other techniques may also be used to heat the conductive heating element, including, for example, inductive heating techniques, conduction techniques, and the use of infrared heating elements as described above with respect to FIGS. 1-3.

In some examples, conductive heating element 222 is also used as a temperature sensor such that the element's temperature is sensed based on a known and predictable correlation between the resistance of the conductive material (e.g., NiChrome) and its temperature. Resistance can be measured by monitoring the voltage across and current through the heating element (i.e., $R=V/I$). This technique allows fast and dynamic temperature determination without the need to add an external temperature sensor (which can cause thermal lag, exhibit variation in measured vs. actual temperature due to poor contact, thermal mass of temperature sensor, etc.) or the complexities of adding a discrete thermal sensor within cavity 211 and the associated control circuitry.

Figure 7:
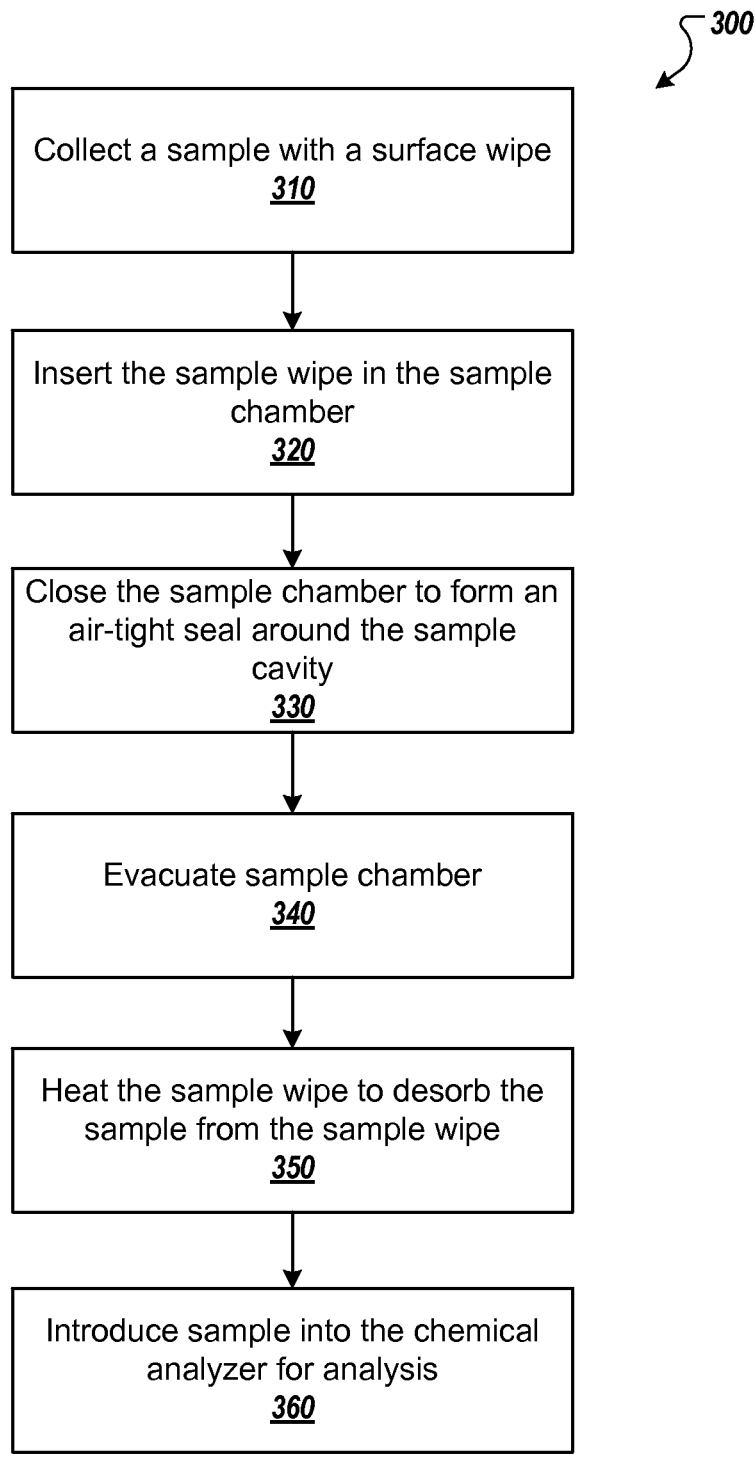
FIG. 7 is a process flow diagram illustrating an example technique for detecting particulates/chemicals captured in or on a collector.

In operation, the detection of particulates/chemicals captured in or on a collector is accomplished, for example, as described in process flow 300 of FIG. 7. In some implementations, the collector may include or be comprised of one or more sorbent materials, including, for example, carbon cloth material, polytetrafuoroethylene (PTFE), polystyrene, cotton, or SPME metal alloy fiber assembly having a polydimethylsiloxane (PDMS) or other coating. A sample is collected (310), for example, by swiping the collector across the surface of a target object or dipping the collector into the target substance. The collector carrying the sample is then inserted into a sample chamber (320) (e.g., sample chamber 110 or 210 of FIGS. 1-6C) of a chemical detection system (e.g., CDS 100 or 200). Upon closing the sample chamber, a substantially air-tight seal is formed around the sample cavity (330). The evacuation phase is then initiated to evacuate the dead volume within the cavity (340), thereby reducing the pressure below atmospheric. After the evacuation phase is complete, the heating phase is initiated to heat the collector 125 (350), thereby causing the sample to be released or desorbed into the chamber. During, or optionally after, the heating phase, the sample is introduced into the chemical analyzer for analysis (360), for example, by opening a valve coupled to an inlet port of the chemical analyzer. In this way, the effective concentration of the sample, as seen by the chemical analyzer, is substantially increased facilitating rapid detection of chemicals at extremely low concentrations.

FIG. 8 is a system diagram of an exemplar arrangement of a chemical detection system (CDS) 300. As shown, the vacuum pump system includes a roughing pump 342 and a turbo pump 344 coupled to chemical analyzer 350 via a portion 336 of vacuum path 330. Roughing pump 342 is also coupled to sample chamber 310 (e.g., sample chamber 110, 210 of FIGS. 1-6C) via a portion 335 of vacuum path 330.

Figure 9:
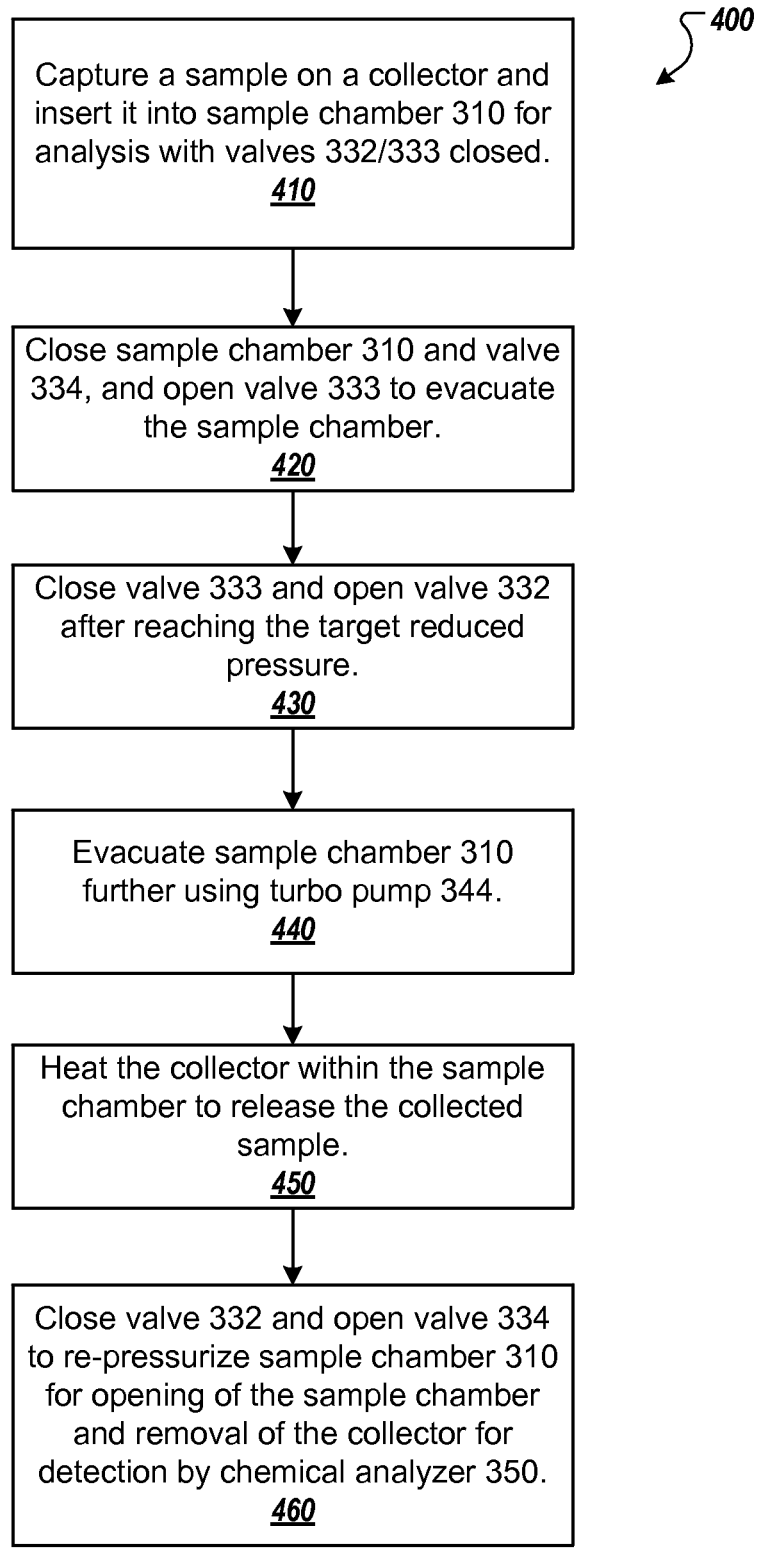
FIG. 9 is an exemplar process flow 400 for using a chemical detection system to transfer a collected sample into a chemical analyzer for analysis.

FIG. 9 illustrates an exemplar process flow 400 for using CDS 300 to transfer a collected sample into a chemical analyzer for analysis. As shown, a sample is captured on a collector and inserted into sample chamber 310 for analysis with valves 332/333 closed (410) and, in some cases, with valve 334 open. Once sample chamber 310 is closed, valve 334 is closed, if open, and valve 333 is opened to evacuate sample chamber 310—i.e., remove the dead volume, including, for example, the background air matrix and any loose contaminants (420). After reaching a target reduced pressure, e.g., 7 Torr, valve 333 is closed and valve 332 is opened (430). Turbo pump 344 is then used to further evacuate sample chamber 310 through portion 336 of vacuum path 330, for example, to $10^{-3}$ Torr (440). During, or after, the evacuation of sample chamber 310, the collector within sample chamber 310 is heated to release the collected sample into chemical analyzer 350 for analysis (450). Valve 332 is then closed and valve 334 is opened to re-pressurize sample chamber 310 for opening of the sample chamber and removal of the collector (460). Other techniques and pressure levels are also possible without changing the scope of this method.

A number of embodiments of the invention have been described. Nevertheless, it will be understood that various modifications may be made without departing from the spirit and scope of the invention. For example, some implementations may include one or more agitators to aid in the release of the sample from the collector. Further, multiple pumps and/or valves may be included in one or more vacuum paths to evacuate the sample chamber and/or to eliminate redundant system components or to facilitate the re-pressurization of sample chamber 110, 210, 310. Accordingly, other embodiments are within the scope of the following claims.

What is claimed is:

1. A method of transferring a sample into a mass spectrometer, the method comprising:
   capturing a surface-wiped sample on a collector;
   receiving, by a sample chamber, the collector carrying the surface-wiped sample, wherein the sample chamber includes two mechanically coupled portions to allow insertion or removal of the collector by at least partially separating the two portions;
   forming, through operation of the two portions, a substantially air-tight cavity within the sample chamber, the cavity containing the collector;
   isolating the sample chamber from the mass spectrometer;
   evacuating the isolated sample chamber using a vacuum pump to reduce an internal pressure of the sample chamber to a level substantially less than atmospheric pressure to increase an effective concentration of the sample;
   heating the collector to release the sample from the collector; and
   introducing the sample into the mass spectrometer from the evacuated sample chamber.

2. The method of claim 1, wherein the collector comprises a sorbent material.

3. The method of claim 1, wherein capturing the sample on the collector comprises wiping a surface of a target object with the collector.

4. The method of claim 1, wherein the collector is pressed against a heating element in the sample chamber.

5. The method of claim 1, wherein heating the collector comprises conducting current through a heating element to induce Joule heating.

6. The method of claim 5, further comprising determining a temperature of the collector based on a measured resistance of the heating element.

7. The method of claim 1, wherein heating the collector comprises conducting current through the collector to induce Joule heating.

8. The method of claim 1, wherein heating the collector comprises emitting radiant energy substantially toward the collector using one or more heating elements.

9. The method of claim 8, wherein heating the collector comprises reflecting the emitted radiant energy substantially toward the collector using a reflective barrier.

10. The method of claim 1, wherein the sample includes a first compound and a second compound different from the first compound, and wherein heating the collector comprises heating the collector to a first temperature during a first time period and a second temperature during a second time period, and wherein release of the first compound is initiated during the first time period, and release of the second compound is initiated during the second time period.

11. The method of claim 10, wherein heating the collector comprises operating a resistive heating element or a radiant heating element at a first power level during the first time period and at a second power level during the second time period.

12. The method of claim 10, wherein heating the collector comprises emitting radiant energy having a first radiant frequency substantially toward the collector during the first time period, and emitting radiant energy having a second radiant frequency substantially toward the collector during the second time period.

13. The method of claim 1, wherein the sample includes a first compound and a second compound, different from the first compound, and wherein evacuating the sample chamber using the vacuum pump to reduce the internal pressure of the sample chamber comprises:
   reducing the internal pressure of the sample chamber to a first level during a first time period; and
   reducing the internal pressure of the sample chamber to a second level during a second time period,
   wherein in response to heating the collector, release of the first compound is initiated during the first time period and release of the second compound is initiated during the second time period.

14. The method of claim 1, wherein the sample includes a first compound and a second compound, different from the first compound, and wherein introducing the sample into the mass spectrometer from the evacuated sample chamber comprises introducing the first compound during a first time period and introducing the second compound during a second time period.

15. A sample analysis system comprising:
   a sample chamber configured to receive a collector carrying a surface-wiped sample, the sample chamber comprising a base and a lid mechanically coupled to each other and operable to at least partially separate from each other to allow insertion or removal of the collector, wherein the base and the lid are configured to form a substantially air-tight cavity that contains the collector within the sample chamber;
   a chemical analyzer coupled to the sample chamber;
   a valve configured to isolate the cavity from the chemical analyzer;
   a vacuum pump coupled to the sample chamber and configured to evacuate the sample chamber to reduce an internal pressure of the sample chamber to a level substantially less than atmospheric pressure to increase an effective concentration of the sample in the cavity after the cavity is isolated from the chemical analyzer by the valve; and a heating element configured to heat the collector to release the sample from the collector into the evacuated sample chamber, wherein the chemical analyzer is configured to receive the sample from the evacuated sample chamber.

16. The system of claim 15, wherein the collector comprises a sorbent material.

17. The system of claim 15, wherein the collector is a wipe.

18. The system of claim 15, wherein the collector is a substrate.

19. The system of claim 15, wherein the collector is a swab.

20. The system of claim 15, wherein the base and lid are configured to press the collector against the heating element.

21. The system of claim 15, wherein the heating element is configured to generate heat via Joule heating.

22. The system of claim 15, wherein the heating element is configured to emit radiant energy substantially toward the collector.

23. The system of claim 22, wherein the emitted radiant energy is of a particular wavelength that preferentially excites a sample of interest.

24. The system of claim 22, further comprising a reflective barrier configured to reflect the emitted radiant energy substantially toward the collector.

25. The system of claim 15, wherein the sample includes a first compound and a second compound different from the first compound, and wherein the heating element is configured to heat the collector to a first temperature during a first time period and a second temperature during a second time period, and wherein release of the first compound is initiated during the first time period, and release of the second compound is initiated during the second time period.

26. The system of claim 25, wherein the heating element is configured to operate at a first power level during the first time period and at a second power level during the second time period.

27. The system of claim 25, wherein the heating element is configured to emit radiant energy having a first radiant frequency substantially toward the collector during the first time period, and is configured to emit radiant energy having a second radiant frequency substantially toward the collector during the second time period.

28. The system of claim 15, wherein the sample includes a first compound and a second compound, different from the first compound, and wherein the vacuum pump is configured to reduce the internal pressure of the sample chamber to a first level during a first time period, and to reduce the internal pressure of the sample chamber to a second level during a second time period, wherein in response to heating of the collector, release of the first compound is initiated during the first time period and release of the second compound is initiated during the second time period.

29. A device for transferring a surface-wiped sample into a chemical analyzer, comprising:
- a base and a lid forming a sample chamber configured to receive a collector carrying the surface-wiped sample, the base and the lid being mechanically coupled to each other and operable to at least partially separate from each other to allow insertion or removal of the collector, wherein the base and the lid are configured to form a substantially air-tight cavity that contains the collector within the sample chamber;
- a vacuum port coupled to a valve configured to isolate the sample chamber from the chemical analyzer; and
- a heating or radiating element configured to heat the collector to release the sample from the collector,
- wherein the device is configured to be coupled to a vacuum pump through the vacuum port, the vacuum pump being operable to evacuate the device to reduce an internal pressure of the device to a level substantially less than atmospheric pressure to increase an effective concentration of the sample in the sample chamber.

* * * * *